United States Patent
Sun

(10) Patent No.: US 8,673,819 B2
(45) Date of Patent: Mar. 18, 2014

(54) SURFACTANT BLENDS USEFUL IN AGRICULTURE

(75) Inventor: Jinxia Susan Sun, Hopewell Junction, NY (US)

(73) Assignee: Akzo Nobel N.V., Arnhem (NL)

( * ) Notice: Subject to any disclaimer, the term of this patent is extended or adjusted under 35 U.S.C. 154(b) by 250 days.

(21) Appl. No.: 13/002,896

(22) PCT Filed: Jul. 3, 2009

(86) PCT No.: PCT/EP2009/058382
§ 371 (c)(1),
(2), (4) Date: Jan. 6, 2011

(87) PCT Pub. No.: WO2010/003889
PCT Pub. Date: Jan. 14, 2010

(65) Prior Publication Data
US 2011/0111961 A1   May 12, 2011

Related U.S. Application Data

(60) Provisional application No. 61/078,894, filed on Jul. 8, 2008.

(30) Foreign Application Priority Data

Sep. 9, 2008   (EP) ..................... 08163976

(51) Int. Cl.
| | |
|---|---|
| A01N 25/30 | (2006.01) |
| A01N 25/00 | (2006.01) |
| A01N 25/02 | (2006.01) |
| A01N 25/04 | (2006.01) |
| A01N 25/16 | (2006.01) |
| A01N 31/14 | (2006.01) |
| A01N 37/00 | (2006.01) |
| A01N 37/02 | (2006.01) |
| A01N 37/06 | (2006.01) |
| A01N 37/10 | (2006.01) |
| A01N 39/02 | (2006.01) |

(52) U.S. Cl.
USPC ........... 504/323; 504/320; 504/358; 504/362; 504/363; 514/546; 514/549; 514/552; 514/571; 514/718; 514/723; 424/405

(58) Field of Classification Search
USPC .......... 424/405; 504/320, 323, 358, 362, 363; 514/546, 549, 552, 571, 718, 723
See application file for complete search history.

(56) References Cited

U.S. PATENT DOCUMENTS

| | | | | |
|---|---|---|---|---|
| 5,674,517 | A * | 10/1997 | Carpenter | 424/405 |
| 6,117,820 | A * | 9/2000 | Cutler et al. | 504/206 |
| 2002/0107149 | A1 | 8/2002 | Volgas et al. | |
| 2003/0013610 | A1 | 1/2003 | Killick et al. | |
| 2003/0148889 | A1 | 8/2003 | Herold et al. | |
| 2004/0014800 | A1 * | 1/2004 | Warrington et al. | 514/383 |

FOREIGN PATENT DOCUMENTS

| | | |
|---|---|---|
| AU | 2004242523 A1 * | 7/2005 |
| WO | WO 00/49873 | 8/2000 |
| WO | WO 02/32227 A1 | 4/2002 |
| WO | WO 2005/011385 A1 | 2/2005 |

OTHER PUBLICATIONS

Dan A. Wolfenbarger, M. J. Lukefahr an d W. L. Lowry, "Toxicity of Surfactants and Surfactant-Insecticide Combinations to the Bollworm, Tobacco Budworm, and Pink Bollworm", Journal of Economic Entomology, 1967, vol. 60, No. 4, 902-904.*
European Search Report for EP Application No. 08163976; Jan. 22, 2009.
International Search Report for PCT Application No. PCT/EP2009/058382; Aug. 6, 209.

* cited by examiner

*Primary Examiner* — John Pak
*Assistant Examiner* — Nathan W Schlientz
(74) *Attorney, Agent, or Firm* — Norris McLaughlin & Marcus, P.A.

(57) ABSTRACT

The present invention teaches a surfactant blend composition of at least one nonionic alkoxylate and at least one sugar-based surfactant, and its use as an adjuvant for pesticides. The pesticidal composition employing the surfactant blend composition of the invention realizes an efficacy that is unexpectedly superior to similar pesticidal compositions which employ only the individual surfactant components. The composition of the present invention is useful as a tank side additive, or as a component in herbicidal formulations. In addition the compositions of the present invention are useful as adjuvants for other pesticides, such as, fungicides, insecticides, plant growth regulators, acaracides and the like.

13 Claims, No Drawings

SURFACTANT BLENDS USEFUL IN AGRICULTURE

The present case was filed under the Patent Cooperation Treaty on Jul. 3, 2009 and claims priority of European application No. 08163976.7 filed Sep. 9, 2008 and U.S. provisional application No. 61/078,894 filed Jul. 8, 2008.

FIELD OF THE INVENTION

The present invention generally relates to surfactant blends comprising at least one alcohol ethoxylate surfactant and at least and at least one ethoxylated sorbitan, sorbitol ester or alkyl glucoside surfactant useful in auxin herbicide herbicides such as 2,4-D and dicamba.

BACKGROUND OF THE INVENTION

Many pesticides require the addition of an adjuvant to the spray mixture to provide wetting and penetrating effects on foliar surfaces. Often that adjuvant is a surfactant, which can perform a variety of functions, such as increasing spray droplet retention on difficult to wet leaf surfaces, or to provide penetration of the herbicide into the plant cuticle. These adjuvants are either provided as a component in an adjuvant formulation or used as an additive in herbicide formulations.

The addition to formulations of certain auxiliaries in order to improve the activity is generally known and agricultural practice. This has the advantage that the amounts of active ingredient in the formulation may be reduced while maintaining the activity of the later, thus allowing costs to be kept as low as possible and any official regulations to be followed. In individual cases it is also possible to widen the spectrum of action since plants, where the treatment with a particular active ingredient without addition was insufficiently successful, can indeed be treated successfully by the addition of certain auxiliaries. Moreover, the performance may be increased in individual cases by a suitable formulation when the environmental conditions are not favorable. The phenomenon that various active ingredients are not compatible with each other in a formulation can therefore also be avoided.

Such auxiliaries are generally also referred to as adjuvants. Frequently, they take the form of surface-active or salt-like compounds. Depending on their mode of action, they can roughly be classified as modifiers, activators, fertilizers, pH buffers and the like. Modifiers affect the wetting, sticking and spreading properties of a formulation. Activators break up the waxy cuticle of the plant and improve the penetration of the active ingredient into the cuticle, both short-term (over minutes) and long-term (over hours). Fertilizers such as ammonium sulfate, ammonium nitrate or urea improve the absorption and solubility of the active ingredient and may reduce the antagonistic behavior of active ingredients. pH buffers are conventionally used for bringing the formulation to an optimal pH.

Regarding the uptake of the active ingredient into the leaf, surface-active substances may act as modifiers and activator. In general, it is assumed that suitable surface-active substances can increase the effective contact area of liquids on leaves by reducing the surface tension. Moreover, surface-active substances can dissolve or break up the epicuticular waxes, thereby facilitating the absorption of the active ingredient. Furthermore, some surface-active substances can also improve the solubility of active ingredients in formulations and thus avoid, or at least delay, crystallization. Finally, they can also affect the absorption of active ingredients in some cases by retaining moisture. Surfactant-type adjuvants are exploited in a number of ways for agro-technical applications. They can be divided into groups of anionic, cationic, nonionic or amphoteric substances.

Substances which are traditionally used as activating adjuvants are petroleum-based oils. More recently, seed extracts, natural oils and their derivatives, for example of soybeans, sunflowers and coconut, have also been employed. However, it is a state of art to choose the right surfactant or surfactant blends to achieve the maximum adjuvancy for the pesticides.

It is therefore an object of the present invention to provide further uses of such adjuvant blends which have increased the pesticide efficacy more than any of the individual components can provide. We have found that this object is achieved by using the blend of alkoxylates and alkyl amines, salts, and quaternary salts as adjuvant and by providing agro-technical compositions comprising these blends.

The present invention therefore relates to the use of the blend of surfactants as adjuvant in the treatment of plants.

SUMMARY OF THE INVENTION

The present invention generally relates to an agricultural adjuvant composition that comprises a surfactant blend, wherein said surfactant blend comprises at least one nonionic alkoxylate, at least one sugar-based surfactant. The sugar-based surfactant component comprises an ethoxylated sorbitan, or sorbitol ester or alkyl glucoside surfactant, or mixtures thereof. Pesticidal compositions that employ the surfactant blend of the invention demonstrate efficacy that is unexpectedly superior to similar pesticidal compositions which employ conventional adjuvants. The composition of the present invention is useful as a tank side additive, or as a component in herbicidal formulations. In addition the compositions of the present invention are useful as adjuvants for other pesticides, such as, fungicides, insecticides, plant growth regulators, acaracides and the like.

DETAILED DESCRIPTION OF THE INVENTION

The present invention provides surfactant blend compositions that are useful as adjuvants for pesticides. The compositions of the present invention provide enhanced pesticide efficacy relative to the individual component.

The blends of the invention have adjuvant increase the uptake of active ingredients by a plant to be treated with the active ingredient. The adjuvant action results in particular in the following aspects in the treatment of plants with one or more active ingredients: higher activity of the active ingredient for a given application rate; lower application rate with a given effect; better uptake of the active ingredient by the plant, in particular via the leaf, and thus advantages for the post-emergence treatment, in particular the spray treatment of plants.

The pesticidal compositions of the inventions employing the surfactant blends described herein have utility in plant cultivation, agriculture and horticulture. A primary use is for controlling undesired plant growth.

The surfactant blend of the present invention comprises at least a nonionic alkoxylate and at least one sugar-based surfactant that comprises ethoxylated sorbitan or sorbitol ester or alkyl glucoside surfactant, or mixtures and/or combinations thereof.

In a one embodiment the nonionic alkoxylate component is an alkoxylated alcohol of the general formula:

$$R^1-O-(C_mH_{2m}O)_x-(C_nH_{2n}O)_y-H \qquad (I)$$

wherein $R^1$ is a straight or branched chain, saturated or unsaturated, substituted or unsubstituted hydrocarbon group having from 4 to 30 carbon atoms, preferably an alkyl group of from 4 to 30 carbon atoms, m is an integer of from 2 to 3, n is an integer of from 2 to 3, x is an integer of from 1-30 and y is an integer of from 0-30.

In another embodiment, $R^1$ is a straight or branched chain, saturated or unsaturated, substituted or unsubstituted alkyl group having from 4 to 22 carbon atoms, m is an integer of from 2 to 3, n is an integer of from 2 to 3, x is an integer of from 1-16 and y is an integer of from 0-16, with the proviso that x+y is 3-12.

In still another embodiment, $R^1$ is a straight or branched chain, saturated or unsaturated, substituted or unsubstituted alkyl group having from 6 to 14 carbon atoms, m is an integer of from 2 to 3, n is an integer of from 2 to 3, x is an integer of from 1-16 and y is an integer of from 0-16, with the proviso that x+y is 3-12.

In yet another embodiment, $R^1$ is a straight or branched chain, saturated or unsaturated, substituted or unsubstituted alkyl group having from 8 to 12 carbon atoms, m is an integer of from 2 to 3, n is an integer of from 2 to 3, x is an integer of from 1-16 and y is an integer of from 0-16, with the proviso that x+y is 3-12.

Generally, the alcohol moiety of the alcohol alkoxylates in accordance with the invention is based on alcohols or alcohol mixtures which have 5 to 30, in another embodiment 8 to 20, and in still another embodiment 10 to 13, carbon atoms. As is known, many of these fatty alcohols are employed in the production of nonionic and anionic surfactants, to which end the alcohols are subjected to suitable functionalization, for example by alkoxylation or glycosidation.

The alcohol moiety of the alkoxylates is optionally branched. When branched, the main chain of the alcohol moiety can have 1 to 4 branchings, it also being possible to use alcohols with a higher or lower degree of branching in a mixture with other alcohol alkoxylates as long as the mean number of branchings of the mixture is in the above-stated range. In general, the branchings independently of one another have 1 to 10, in another embodiment 1 to 6, and in still another embodiment 1 to 4, carbon atoms. Particular branchings are methyl, ethyl, n-propyl or isopropyl groups. In accordance with one embodiment, the alcohol moieties on which the alkoxylates are based thus have an average of at least two terminal methyl groups.

In one embodiment, alcohol alkoxylates of the formula (I) are used in which m=2 and the value of x is greater than zero. These are alcohol alkoxylates of the ethylene oxide (EO) type, which include mainly alcohol ethoxylates (m=2; x>zero; y=zero) and alcohol alkoxylates with an EO block bonded to the alcohol moiety (m=2; x>zero; y>zero). In addition to alcohol alkoxylates with an EO block bonded to the alcohol moiety, the following can also be employed: EO/PO block alkoxylates (m=2; x>zero; y>zero; n=3), and EO/PO block alkoxylates (m=2; x>zero; y>zero; n=5).

In another embodiment, EO/PO block alkoxylates are contemplated, wherein the EO:PO ratio (x:y) is 1:1 to 4:1, in particular 1.5:1 to 3:1. In this context, the degree of ethoxylation (value of x) is from about 1 to 20, in another embodiment from about 2 to 15, and in still another embodiment from 4 to 10, and the degree of propoxylation (value of y) is from about 1 to 20, in another embodiment from about 1 to 8, and in still another embodiment from 2 to 5. The total degree of alkoxylation, i.e. the total of EO and PO units, is generally from about 2 to 40, in another embodiment from 3 to 25, and in still another embodiment 6 to 15.

Furthermore EO/PO block alkoxylates in which the EO:PO ratio (x:y) is 2:1 to 25:1, in another embodiment 4:1 to 15:1 are also useful. In this context, the degree of ethoxylation (value of x) is from about 1 to 50, in another embodiment from about 4 to 25, and in still another embodiment from about 6 to 15, and the degree of propoxylation (value of y) is generally from about 0.5 to 20, in another embodiment from about 0.5 to 4, and in still another embodiment from about 0.5 to 2. The total degree of alkoxylation, i.e. the total of EO and PO units, is generally from about 1.5 to 70, in another embodiment 4.5 to 29, and in still another embodiment 6.5 to 17.

In accordance with a further particular embodiment, alcohol alkoxylates of the formula (I) are used in which n=2, and the values of x and y are both greater than zero. Again, these alcohol alkoxylates take the form of the EO type, with the EO block being bonded terminally, however. These include mainly PO/EO block alkoxylates (n=2; x>zero; y>zero; m=3) and PO/EO block alkoxylates (n=2; x>zero; y>zero; m=5). In one embodiment, PO/EO block alkoxylates are those in which the PO:EO ratio (x:y) is 1:10 to 3:1, in another embodiment from about 1.5:1 to 1:6. In this context, the degree of ethoxylation (value of y) is generally from about 1 to 20, in another embodiment from about 2 to 15, and in still in still another embodiment from about 4 to 10, and the degree of propoxylation (value of x) is generally from about 0.5 to 10, in another embodiment from about 0.5 to 6, and in still another embodiment from about 1 to 4. The total degree of alkoxylation, i.e. the total of EO and PO units is generally from about 1.5 to 30, in another embodiment from about 2.5 to 21, and in yet another embodiment from about 5 to 14.

In another embodiment, the invention relates to PO/EO block alkoxylates in which the PO:EO ratio (x:y) is from about 1:50 to 1:3, in another embodiment from about 1:25 to 1:5. In this context, the degree of propoxylation (value of x) is generally from about 0.5 to 20, in another embodiment from about 0.5 to 4, and in still another embodiment from about 0.5 to 2, and the degree of ethoxylation (value of y) is generally from about 3 to 50, in another embodiment from about 4 to 25, and in yet another embodiment from about 5 to 15. The total degree of alkoxylation, i.e. the total of EO and PO units, is generally from about 3.5 to 70, in another embodiment from about 4.5 to 45, and in yet another embodiment from about 5.5 to 17.

In still another embodiment, the alcohol alkoxylates of the invention are based on primary, α-branched alcohols of the formula (I) wherein $R^1$ is a $C_1$-$C_{26}$-alkyl group. Another class of useful branched alcohol alkoxylates are those alkoxylates based on 2-propylheptanol. These include, in particular, alcohol alkoxylates of the formula (I) in which R is a 2-propylheptyl radical. Such alcohols are also referred to as Guerbet alcohols. Alkoxylates that are based on Guerbet alcohols are mainly alkoxylates of the EO type. Particularly preferred are ethoxylates with a degree of ethoxylation of 1 to 50, preferably 2 to 20, in particular approximately 3 to 10. The correspondingly ethoxylated 2-propylheptanols may be mentioned especially among these.

In yet another embodiment, the alcohol alkoxylates are based on $C_{13}$—OXO alcohols. As a rule, the term "$C_{13}$—OXO alcohol" refers to an alcohol mixture whose main component is formed by at least one branched $C_{13}$-alcohol (isotridecanol). Such $C_{13}$-alcohols include, in particular, tetramethylnonanols, for example 2,4,6,8-tetramethyl-1-nonanol or 3,4,6,8-tetramethyl-1-nonanol and furthermore ethyldimethylnonanols such as 5-ethyl-4,7-dimethyl-1- nonanol. Suitable C13-alcohol mixtures can generally be obtained by hydrogenation of hydroformylated trimeric butene.

Some nonionic alkoxylates having utility in the context of the present invention are listed below
C10-12 alcohol (10 EO) Ethoxylate
Tridecyl alcohol (6EO) Ethoxylate
C 10 alcohol (5 EO) Ethoxylate
C8 alcohol Ethoxylate (4 EO)
C9-11 alcohol Ethoxylate (4 EO)
Isodecyl alcohol (7 EO) Ethoxylate The second component of the surfactant blend of the invention comprises and at least one ethoxylated sorbitan or sorbitol ester or alkyl glucoside surfactant, or mixtures thereof. If the $2^{nd}$ component of the surfactant blend of the invention is sorbitan based surfactant, the following polyethylene sorbitans are particularly useful:

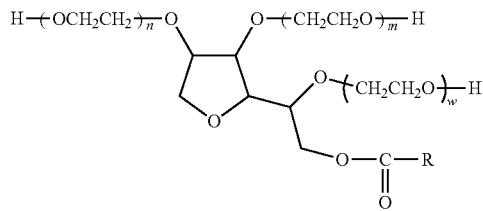

where R is selected from a straight or branched chain, saturated or unsaturated, substituted or unsubstituted $C_6$ to $C_{22}$ hydrocarbon group, and each of n+m+w is independently selected from an integer of from about 10 to 30, in another embodiment of from about 10-20.

If the $2^{nd}$ component is alkyl glucoside based, the following alkyl glycoside of the formula is particularly useful:

$RCH_2O(G)xH$, wherein R is an alkyl group having a total of 4-22 carbon atoms and selected from a straight or branched chain, saturated or unsaturated, substituted or unsubstituted hydrocarbon group; G is a monosaccharide; and x is 1-5.

In one embodiment, the surfactant blend of the invention comprises
Polysorbate
Sorbitan monooleate
Alkyl glucoside Generally, the ratio of the at least a nonionic alkoxylate and sugar-based surfactant comprising at least one ethoxylated sorbitan or sorbitol ester or alkyl glucoside surfactant, or mixtures thereof is in the range of 99:1 and 1:99 by weight; in another embodiment, from 25:75 to 75:25; and in still another embodiment 45:65 to 65:45. In most applications, a ratio that approximate a 50:50 blend of the two components performs particularly well.

For the purposes of the present description, the term "alkyl" encompasses straight-chain or branched hydrocarbon groups such as methyl, ethyl, n-propyl, i-propyl, n-butyl, i-butyl, sec-butyl, t-butyl, n-pentyl, n-hexyl, n-octyl, 2-ethylhexyl, n-nonyl, isononyl, n-decyl, isodecyl, n-undecyl, isoundecyl, n-dodecyl, isododecyl, n-tridecyl, isotridecyl, stearyl, n-eicosyl. In another embodiment-unless otherwise specified—having 1 to 8, in particular 1 to 6 and in another embodiment 1 to 4 carbon atoms in the case of short-chain radicals and from about 5 to 30, in particular 12 to 24 and in another embodiment from about 8 to 20 carbon atoms in the case of long-chain radicals. The branched long-chain radicals include mainly 2-ethylhexyl, isononyl, isodecyl such as 2-propylheptyl, isoundecyl, isododecyl, and isotridecyl such as 2,4,8-tetramethyl-1-nonyl, 3,4,6,8-tetramethyl-1-nonyl and 5-ethyl-4,7-dimethyl-1-nonyl.

The compositions of the present invention also can include a variety of optional ingredients such as auxiliary surfactants, solvents, diluents, delayed release agents, pH buffers, antifoams, and the like.

Auxiliary Surfactants

Suitable auxiliary surfactants include, but are not limited to nonionic, cationic, amphoteric, polymeric surfactants, and the like.

The nonionic surfactants include, for example, further alkoxylates, mainly ethoxylates, and nonionic surfactants, in particular fatty alcohol polyoxyethylene esters, for example lauryl alcohol polyoxyethylene ether acetate, alkyl polyoxyethylene ethers and alkyl polyoxypropylene ethers, for example of linear fatty alcohols, alkylaryl alcohol polyoxyethylene ethers, for example octylphenol polyoxyethylene ether, alkoxylated animal and/or vegetable fats and/or oils, for example corn oil ethoxylates, castor oil ethoxylates, tallow fat ethoxylates, glycerol esters such as, for example, glycerol monostearate, fatty alcohol alkoxylates and oxo alcohol alkoxylates, in particular of the linear type $R_5O$—$(R_3O)$ $(R_4O)sR_{20}$ where $R_3$ and $R_4$ independently of one another =$C_2H_4$, $C_3H_6$, $C_4H_8$ and R20=H, or $C_1$-$C_{12}$-alkyl, $R_5$=$C_3$-$C_{30}$-alkyl or $C_6$-$C_{30}$-alkenyl, r and s independently of one another are 0 to 50, where one of these must be other than 0, and oleyl alcohol polyoxyethylene ether, alkylphenol alkoxylates such as, for example, ethoxylated isooctylphenol, octylphenol or nonylphenol, tributylphenyl polyoxyethylene ethers, fatty amine alkoxylates, fatty acid amide alkoxylates and fatty acid diethanolamide alkoxylates, in particular their ethoxylates, sugar surfactants, sorbitol esters such as, for example, sorbitan fatty acid esters (sorbitan monooleate, sorbitan tristearate), polyoxyethylene sorbitan fatty acid esters, alkylpolyglycosides, N-alkylgluconamides, 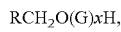-alkylmethyl sulfoxides, alkyldimethylphosphine oxides such as, for example, tetradecyldimethylphosphine oxide.

The amphoteric surfactants include, for example, sulfobetaines, carboxybetaines and alkyldimethylamine oxides, for example tetradecyldimethylamine oxide.

The polymeric surfactants include, for example, di-, tri- and multi-block polymers of the type (AB), ABA and BAB, for example optionally end-capped ethylene oxide/propylene oxide block copolymers, for example ethylenediamine-EO/PO block copolymers, polystyrene block polyethylene oxide, and AB comb polymers, for example polymethacrylate comb polyethylene oxide.

Further surfactants to be mentioned in the present context by way of example are perfluoro surfactants, silicone surfactants, for example polyether-modified siloxanes, phospholipids such as, for example lecithin or chemically modified lecithins, amino acid surfactants, for example N-lauroylglutamate, and surface-active homo- and copolymers, for example polyvinylpyrrolidone, polyacrylic acids in the form of their salts, polyvinyl alcohol, polypropylene oxide, polyethylene oxide, maleic anhydride/isobutene copolymers and vinylpyrrolidone/vinyl acetate copolymers. Unless specified, the alkyl chains of the abovementioned surfactants are linear or branched radicals, usually having 8 to 20 carbon atoms.

Auxiliary surfactants, if present, generally amount to less than 20% by weight, preferably less than 15% by weight and in particular less than 5% by weight of the total weight of the surfactant blend composition of the invention.

Further Auxiliaries

Suitable auxiliaries are chosen in the customary manner by the skilled worker to suit the requirements. For example, further auxiliaries are selected from among solvents or diluents; emulsifiers, delayed-release agents, pH buffers, antifoams, and the like.

Besides water, the compositions may comprise further solvents of soluble components or diluents of insoluble components of the composition. Examples which are useful in principle are mineral oils, synthetic oils, vegetable oils and animal oils, and low-molecular-weight hydrophilic solvents such as alcohols, ethers, ketones and the like. Those which must therefore be mentioned are, firstly, aprotic or apolar solvents or diluents, such as mineral oil fractions of medium to high boiling point, for example kerosene and diesel oil, furthermore coal tar oils, hydrocarbons, paraffin oils, for example $C_8$- to C30 hydrocarbons of the n- or isoalkane series or mixtures of these, optionally hydrogenated or partially hydrogenated aromatics or alkylaromatics from the benzene or naphthalene series, for example aromatic or cycloaliphatic C7- to C18-hydrocarbon compounds, aliphatic or aromatic carboxylic acid esters or dicarboxylic acid esters, or fats or oils of vegetable or animal origin, such as mono-, di- and triglycerides, in pure form or in the form of a mixture, for example in the form of oily extracts of natural materials, for example olive oil, soya oil, sunflower oil, castor oil, sesame seed oil, corn oil, groundnut oil, rapeseed oil, linseed oil, almond oil, castor oil, safflower oil, and their raffinates, for example hydrogenated or partially hydrogenated products thereof and/or their esters, in particular the methyl and ethyl esters.

Examples of $C_8$- to C30-hydrocarbons of the n- or isoalkane series are n- and isooctane, -decane, -hexadecane, -octadecane, -eicosane, and preferably hydrocarbon mixtures such as liquid paraffin (technical-grade liquid paraffin may comprise up to approximately 5% aromatics) and a C18-C24 mixture which is commercially available from Texaco under the name Spraytex oil.

The aromatic or cycloaliphatic $C_7$ to $C_{18}$ hydrocarbon compounds include, in particular, aromatic or cycloaliphatic solvents from the series of the alkylaromatics. These compounds may be unhydrogenated, partially hydrogenated or fully hydrogenated. Such solvents include, in particular, mono-, di- or trialkylbenzenes, mono-, di- or trialkyl-substituted tetralins and/or mono-, di-, tri- or tetraalkyl-substituted naphthalenes (alkyl is preferably $C_1$-$C_6$-alkyl). Examples of such solvents are toluene, o-, m-, p-xylene, ethylbenzene, isopropylbenzene, tert-butylbenzene and mixtures, such as the Shell products sold under the names Solvesso, for example Solvesso 100, 150 and 200.

Examples of suitable monocarboxylic esters are oleic esters, in particular methyl oleate and ethyl oleate, lauric esters, in particular 2-ethylhexyl laurate, octyl laurate and isopropyl laurate, isopropyl myristate, palmitic esters, in particular 2-ethylhexyl palmitate and isopropyl palmitate, stearic esters, in particular n-butyl stearate and 2-ethylhexyl 2-ethylhexanoate. Examples of suitable dicarboxylic esters are adipic esters, in particular dimethyl adipate, di-n-butyl adipate, di-n-octyl adipate, di-iso-octyl adipate, also referred to as bis(2-ethylhexyl) adipate, di-n-nonyl adipate, diisononyl adipate and ditridecyl adipate; succinic esters, in particular di-n-octyl succinate and diisooctyl succinate, and di(isononyl)cyclohexane 1,2-dicarboxylate.

Generally, the above-described aprotic solvents or diluents amount to less than 80% by weight, preferably less than 50% by weight and in particular less than 30% by weight of the total weight of the composition.

Some of these aprotic solvents or diluents may also have adjuvant properties, that is to say in particular synergistic properties. This applies in particular to said mono- and dicarboxylic esters. From this point of view, such adjuvants, perhaps in the form of a part of a further formulation (stand-alone product), may also be mixed with the alcohol alkoxylates according to the invention or with compositions comprising them at an expedient point in time, as a rule shortly prior to application.

Secondly, solvents or diluents which must be mentioned are protic or polar solvents or diluents, for example $C_2$-$C_8$-monoalcohols such as ethanol, propanol, isopropanol, butanol, isobutanol, tert-butanol, cyclohexanol and 2-ethylhexanol, C3-Cs-ketones such as diethyl ketone, t-butyl methyl ketone and cyclohexanone, and aprotic amines such as N-methyl- and N-octylpyrrolidone.

Generally, the above-described protic or polar solvents or diluents amount to less than 80% by weight, preferably less than 50% by weight and in particular less than 30% by weight of the total weight of the composition.

Sedimentation inhibitors may also be used, in particular for suspension concentrates. Their main purpose is rheological stabilization. Products which must be mentioned in this context are, in particular, mineral products, for example bentonites, talcites and hectorites.

Other additions which may be useful can be found for example among mineral salt solutions which are employed for alleviating nutritional and trace element deficiencies, non-phytotoxic oils and oil concentrates, anti-drift agents, antifoams, in particular the silicone type products, for example Silicon SL, which is sold by Wacker, and the like. The formulations may be present in the form of an emulsifiable concentrate (EC), a suspoemulsion (SE), an oil-in-water emulsion (O/W), a water-in-oil emulsion (W/O), an aqueous suspension concentrate, an oil suspension concentrate (OD), a microemulsion (ME) and the like.

The compositions can be prepared in the manner known per se. To this end, at least some of the components are combined. It must be taken into consideration that products, in particular commercially available products, can be used whose constituents may contribute to different components. For example, a specific surfactant can be dissolved in an aprotic solvent, so that this product can contribute to different components. Furthermore, it is also possible in some circumstances for minor amounts of less desired substances to be introduced together with commercially available products. As a rule, the products which have been combined to a mixture must then be mixed thoroughly with each other to give a homogeneous mixture.

The compositions of the invention are diluted in the customary manner prior to use to obtain a form which is suitable for application. Dilution with water or else aprotic solvents, for example by the tank mix method, is preferred. The use in the form of a slurry preparation is preferred. The application may be pre- or post-emergence. Post-emergence application results in particular advantages.

The compositions of the invention also optionally include ingredients for use herein which are herbicide, especially acid functional ones, e.g., compounds that contain at least one carboxylic, sulfonic or phosphonic acid group which is in the form of the free acid or a salt or ester thereof. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of herbicide employed in compositions of the invention varies with the type of pesticide employed. More specific examples of pesticide compounds that can be used with the compositions of the invention are phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, cyclohexanediones, aryloxyphenoxypropanoates, dichlobenil, isoxaben, and bipyridylium compounds. Examples of these compounds and their esters that present these characteristics and which are considered to be covered by present invention are:

(R—COO)$_n$—R' wherein R—COO represents an acetate of one of the following acids:

arylalanines such as
N-benzoyl-N-(3,4-dichlorophenyl)-DL-alanine (benzoylprop), and
N-benzoyl-N-(3-chloro-4-fluorophenyl)-D-alanine (flamprop);

aryloxyphenoxypropionic acids such as
(RS)-2-[4-(3,5-dichloro-2-pyridyloxy)phenoxy]propionic acid (chlorazifop),
(R)-2-[4-(4-cyano-2-fluorophenoxy)phenoxy]propionic acid (cyhalofop),
(RS)-2-[4-(2,4-dichlorophenoxy)phenoxy]propionic acid (diclofop),
(RS)-2-[4-(6-chloroquinoxalin-2-yloxy)phenoxy]propionic acid (quizalofop),
(R)-2-[4-(6-chloroquinoxalin-2-yloxy)phenoxy]propionic acid (quizalofop-P), and
(RS)-2-[4-($\alpha,\alpha,\alpha$-trifluoro-p-tolyloxy)phenoxy]propionic acid (trifop);

benzoic acids such as
3,6-dichloroanisic acid (dicamba), and
3,5,6-trichloroanisic acid (tricamba);

cyclohexene oximes such as
(E)-(RS)-3-[1-(allyloxyimino)butyl]-4-hydroxy-6,6-dimethyl-2-oxocyclohex-3-enecarboxylic acid (all oxydim);

dicarboximides such as
(Z)-2-chloro-3-[2-chloro-5-(cyclohex-1-ene-1,2-dicarboximido)phenyl]acrylic acid (cinidon), and
[2-chloro-5-(cyclohex-1-ene-1,2-dicarboximido)-4-fluorophenoxy]acetic acid (flumiclorac);

imidazolinones such as
2-[4,5-dihydro-4-methyl-4-(1-methylethyl)-5-oxo-1H-imidazol-2-yl]-4(or 5)-methylbenzoic acid (imazamethabenz),
(RS)-2-(4-isopropyl-4-methyl-5-oxo-2-imidazolin-2-yl)quinoline-3-carboxylic acid (imazaquin), and
(RS)-5-ethyl-2-(4-isopropylmethyl-5-oxo-2-imidazolin-2-yl)nicotinic acid (imazethapyr);

nitrophenyl ethers such as
5-(2-chloro-$\alpha,\alpha,\alpha$-trifluoro-p-tolyloxy)-2-nitrobenzoic acid (acifluorfen),
5-(2,4-dichlorophenoxy)-2-nitrobenzoic acid (bifenox),
O-[5-(2-chloro-$\alpha,\alpha,\alpha$-trifluoro-p-tolyloxy)-2-nitrobenzoyl] glycolic acid (fluoroglycofen), and
O-[5-(2-chloro-$\alpha,\alpha,\alpha$-trifluoro-p-tolyloxy)-2-nitrobenzoyl]-DL-lactic acid (lactofen);

phenoxyacetic acids such as
(2,4-dichlorophenoxy)acetic acid (2,4-D),
4-chlorophenoxyacetic acid (4-CPA), and
(4-chloro-2-methylphenoxy)acetic acid (mcpa);

phenoxybutyric acids such as
4-(2,4-dichlorophenoxy)butyric acid (2,4-DB), and
4-(4-chloro-o-tolyloxy)butyric acid (mcpb);

phenoxypropionic acids such as
(RS)-2-(2,4-dichlorophenoxy)propionic acid (dichlorprop),
(R)-2-(2,4-dichlorophenoxy)propionic acid-(dichlorprop-P),
(R)-2-(4-chloro-o-tolyloxy)propionic acid(mecoprop-P);

picolinic acids such as
3,6-dichloropyridine-2-carboxylic acid (clopyralid),
4-amino-3,5-dichloro-6-fluoro-2-pyridyloxyacetic acid (fluoroxypyr), and
4-amino-3,5,6-trichloropyridine-2-carboxylic acid (picloram);

pyrazolphenyls such as
5-[4-bromo-1-methyl-5-(trifluoromethyl)pyrazol-3-yl]-2-chloro-4-fluorobenzoic acid (fluazolate), and
2-chloro-5-(4-chloro-5-difluoromethoxy-1-methylpyrazol-3-yl)-4-fluorophenoxyacetic acid (pyraflufen);

pyridazinones such as
2-chloro-5-[1,6-dihydro-5-methyl-6-oxo-4-(trifluoromethyl)pyridazin-1-yl]-4-fluorophenoxyacetic acid (flufenpyr),
5-bromo-1,6-dihydro-6-oxo-1-phenylpyridazin-4-yloxamic acid (oxapyrazon), and
(RS)-hexahydro-4-hydroxy-3,6-dioxopyridazin-4-ylacetic acid (pydanon);

pyridines such as
2-difluoromethyl-5-(4,5-dihydro-1,3-thiazol-2-yl)-4-isobutyl-6-trifluoromethylnicotinic acid (thiazopyr), and
3,5,6-trichloro-2-pyridyloxyacetic acid (triclopyr); pyrimidinyloxybenzoics such as
2,6-bis(4,6-dimethoxypyrimidin-2-yloxy)benzoic acid (bispyribac), and
2-(4,6-dimethoxypyrimidin-2-yloxy)-6-(1-methoxyiminoethyl)benzoic acid (pyriminobac)
2-chloro-6-(4,6-dimethoxypyrimidin-2-ylthio)benzoic acid (pyrithiobac); quinolinecarboxylics such as
3,7-dichloroquinoline-8-carboxylic acid (Quinclorac), and
7-chloro-3-methylquinoline-8-carboxylic acid (Quinmerac);
sulfonanilides such as
3-chloro-2-(5-ethoxy-7-fluoro[1,2,4]triazolo[1,5-c]pyrimidin-2-ylsulfonamido)benzoic acid (Cloransulam);

triazolones such as
(RS)-2-chloro-3-{2-chloro-5-[4-(difluoromethyl)-4,5-dihydro-3-methyl-5-oxo-1H-1,2,4-triazol-1-yl]-4-fluorophenyl)propionic acid (Carfentrazone);

unclassified such as
[2-chloro-4-fluoro-5-(5,6,7,8-tetrahydro-3-oxo-1H,3H-[1,3,4]thiadiazolo[3,4-a]pyridazin-1-ylideneamino)phenylthio]acetic acid (Fluthiacet);

uracils such as
1-(allyloxycarbonyl)-1-methylethyl 2-chloro-5-[1,2,3,6-tetrahydro-3-methyl-2,6-dioxo-4-(trifluoromethyl)pyrimidin-1-yl]benzoic acid (Butafenacil), and
2-chloro-5-(1,2,3,6-tetrahydro-3-methyl-2,6-di-oxo-4-trifluoromethylpyrimidin-1-yl)benzoicacid (flupropasil);

Phosphinic acid derivatives such as
4-[hydroxyl(methyl)phosphinoyl]-DL-homoalanine (glufosinate) and the salts thereof;

Sulfonylurea derivatives such as
3-chloro-5-(4,6-dimethoxypyrimidin-2-ylcarbamoylsulfamoyl-1-methylpyrazole carboxylic acid (Halosulfuron) EP-A0282613,
3-[(4,6-dimethoxypyrimidin-2-ylcarbamoyl)sulfamoyl]-6-(trifluoromethyl)nicotinic acid (Flupyrsulfuron) see Brighton Crop Prot. Conf. Weeds, 1995, p. 49), 2-[[[[(4,6-dimethoxy-2-pyrimidinyl)amino]carbonyl]
   amino]sulfonyl]-4-[[(methylsulfonyl)amino]methyl]benzoic acid (Mesosulfuron),
3-chloro-5-(4,6-dimethoxypyrimidin-2-ylcarbamoylsulfamoyl)-1-methylpyrazole-4-carboxylicacid (EP-A 0 282 613),
5-(4,6-dimethylpyrimidin-2-yl-carbamoylsulfamoyl)-1-(2-pyridyl)pyrazole-4-carboxylic acid (NC-330, see Brighton Crop Prot. Conference 'Weeds' 1991, Vol. 1, p 45 et seq.),
2-[4-dimethylamino-6-(2,2,2-trifluoroethoxy)-1,3,5-triazin-2-ylcarbamoylsulfamoyl]-m-toluic acid(Triflusulfuron),
3-(4-ethyl-6-methoxy-1,3,5-triazin-2-yl)-1-(2,3-dihydro-1,1-dioxo-2-methylbenzo[b]thiophen-7-sulfonyl)urea (EP-A 0 796 83);
and urea derivatives
and R' is an alkyl group of a polyol containing two or more carbon atoms, which may be linear or branched, saturated or unsaturated, substituted or unsubstituted, optionally having heteroatoms such as N or O within the group.

Manufacture

Each of the components of the blend of the invention are commercially available and/or their manufacture is known in the art. The pesticidal actives are also well known and commercially available.

Use

The nonionic alkoxylates and at least one ethoxylated sorbitan or sorbitol ester or alkyl glucoside surfactant blends of the present invention are primarily are intended for use in the agricultural field as adjuvants for pesticidal actives, especially acid functional pesticides containing aqueous end-use formulations. The compositions of the present invention are added directly to a spray tank along with an acid functional pesticide, or as part of a pesticide formulation. They are used in effective amount, that is, an amount which is sufficient to cause the pesticide to function effectively in the formulation. When used as a tankside additive, the compositions of this invention should be present at weight concentrations between 0.01% and 5.0%, preferably between 0.025% and 0.5%, but in "in can" formulations, the compositions of the present invention may be present at concentrations that will deliver between 0.01% and 5.0% to the final use dilution, preferably between 0.025% and 0.5%, of the final use dilution.

The novel nonionic alkoxylates and ethoxylated sorbitan and sorbitol ester or alkyl glucoside surfactant blend compositions of the present invention may also be used generally as surface active agents in aqueous formulation where there is an acid functionalized component, including, but not limited to, surfactants, wetting agents and softeners for textiles, as flowing and leveling agents in coatings, in hair care products and creams for personal care applications and as anti-static agents and softeners for laundry products. The use according to the invention also encompasses the use of the surfactant blends according to the invention as "stand-alone" products. To this end, the blends are prepared in a suitable manner and added shortly before use to the composition to be applied.

Particular advantages result mainly when carrying out a spray treatment. A customary spray mixture to be used as a tank mix involves diluting the compositions according to the invention which already comprise the surfactant blend—or further plant treatment products with addition of the surfactant blends as "stand-alone" product—with water to apply, per hectare, approximately 0.01 to 10, preferably approximately 0.05 to 5, in particular 0.1 to 1, kg of the surfactant blend according to the invention.

For the purposes of the present description, quantities generally refer to the total weight of a composition, unless otherwise specified. As a rule, the term "essentially" refers in accordance with the invention to a percentage of at least 80%, preferably at least 90% and in particular at least 95%.

When the novel surfactant blend are used with one or more herbicidal acid or their ester, the mixture compositions according to the invention have an outstanding herbicidal activity against monocotyledonous and dicotyledonous weeds which are listed on the label as easy or tough to control species, and as such, will be active against many crop plants.

The following non-limiting examples are presented to further illustrate and explain the present invention. Unless otherwise indicated, all parts and percentages are by weight, and are based on the weight at the particular stage of the processing being described.

EXAMPLE 1

Herbicidal Efficacy of the 2,4-D amine Formulations

Table 1 provides the compositions of the surfactant blends information of this invention. Surfactants Reference MW Wt %

TABLE 1

Compositions of surfactant blends in the invention

| Surfactant Blend | Component 1 | Component 2 |
|---|---|---|
| Blend | C 10 alcohol, (7 EO) ethoxylated (50%)[1] | polyoxyethylene sorbitan monolaurate (50%)[2] |

[1]Trade name of Adsee ® LowFoam A, product of Akzo Nobel
[2]Trade name Canarcel TW20, product of Oxiteno.

The surfactant blend(s) described in Table 1 were applied by the tank mix method together with 2,4-D amine salt (465 g/l). The application rate per ha was 0.1250 lb 2,4-D amine salt ai/A and 0.25% of surfactant blends according to the invention or 0.25% comparative adjuvant Activator 90 (alkylphenol ethoxylate, alcohol ethoxylate and tall oil fatty acid, (Loveland). The herbicidal effect was assessed in a greenhouse experiment. The test plant used was alfalfa (*Medicago sativa*).

The plants were sown directly to the pot. When the active ingredient was applied, the plants were 20-30 cm in height. The test containers used were plastic pots containing potting mixture. The surfactants were applied by the tank mix method by spray application post-emergence in an automated spray cabinet with a water application rate of 200 liters per hectare. Evaluation was carried out using a scale of from 0% to 100%. 0% means no damage, 100% means complete damage. The results of the assessment are compiled in table 2 and which follow.

TABLE 2

| | | | Alfalfa | Alfalfa | | |
| | 2,4-D amine | Adjuvant | (1WAT[1]) | (2WAT) | Alfalfa | Alfalfa |
| Adjuvant | (lb/A) | (% wt) | % of | Control | (3WAT) | (4WAT) |
| --- | --- | --- | --- | --- | --- | --- |
| Canarcel TW20 | 0.1250 | 0.25 | 27.5 | 42.5 | 37.5 | 47.5 |
| Adsee Lowfoam A | 0.1250 | 0.25 | 32.5 | 52.5 | 57.5 | 72.5 |
| Blend A | 0.1250 | 0.25 | 37.5 | 57.5 | 67.5 | 80 |
| None | 0.1250 | 0 | 12.5 | 17.5 | 20.0 | 22.5 |

The effect of adjuvant blends on 2,4-D amine efficacy in Alfalfa

[1]Week after treatment
[2]: Control (5)

It can be seen clearly that formulations with surfactant blends according to the invention are considerably more effective than the comparative formulation with the individual surfactant components according to the invention.

I claim:

1. An aqueous herbicidal formulation consisting essentially of at least one acid functional phenoxy herbicide and a weight concentration of from 0.01 to 5% based on a total weight of the formulation of at least one adjuvant composition, wherein the at least one adjuvant composition is a blend of:
    at least one alkoxylated nonionic surfactant, and
    at least one ethoxylated sorbitan,
    wherein said at least one alkoxylated nonionic surfactant is selected from the group consisting of C10-12 alcohol (10 EO) ethoxylate, tridecyl alcohol (6EO) ethoxylate, C10 alcohol (5 EO) ethoxylate, C8 alcohol (4 EO) ethoxylate, C9-11 alcohol (4 EO) ethoxylate, isodecyl alcohol (7 EO) ethoxylate and mixtures thereof; and
    wherein said at least one ethoxylated sorbitan is of the formula:

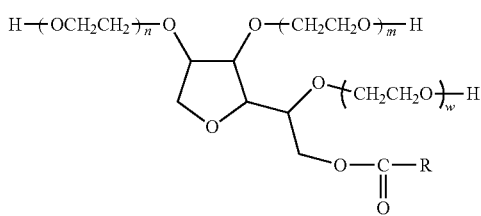

where R is selected from the group consisting of a straight or branched chain, saturated or unsaturated, substituted or unsubstituted $C_6$ to $C_{22}$ hydrocarbon group, and n+m+w is from about 10 to 30.

2. The formulation of claim 1, wherein said adjuvant composition is present at weight concentrations from 0.025% to 0.5%.

3. The formulation of claim 1 wherein the weight ratio of alkoxylated alcohol to ethoxylated sorbitan is from 1:99 to 99:1.

4. The formulation of claim 1 wherein the acid functional phenoxy herbicide is selected from the group consisting of phenoxy acetic acids, phenoxy propionic acids, phenoxy butyric acids and mixtures thereof.

5. The formulation of claim 1 wherein the weight ratio of alkoxylated alcohol to ethoxylated sorbitan is from 25:75 to 75:25.

6. The formulation of claim 5 wherein the weight ratio of alkoxylated alcohol to ethoxylated sorbitan is from 45:65 to 65:45.

7. A method for treating plants which comprises contacting said plants with an effective amount of the formulation of claim 1.

8. A method of improving the efficacy of an aqueous herbicidal formulation of one or more acid functional phenoxy herbicidal actives, said method consisting essentially of adding to said formulation a blend of:
    at least one alkoxylated nonionic surfactant, and
    at least one ethoxylated sorbitan,
    to a weight concentration of from 0.01 to 5% based on a total weight of the formulation,
    wherein said at least one alkoxylated nonionic surfactant is selected from the group consisting of C10-12 alcohol (10 EO) ethoxylate, tridecyl alcohol (6EO) ethoxylate, C10 alcohol (5 EO) ethoxylate, C8 alcohol (4 EO) ethoxylate, C9-11 alcohol (4 EO) ethoxylate, isodecyl alcohol (7 EO) ethoxylate and mixtures thereof; and
    wherein said at least one ethoxylated sorbitan is of the formula:

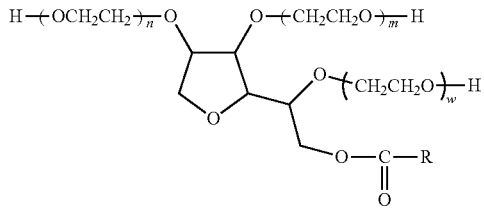

where R is selected from the group consisting of a straight or branched chain, saturated or unsaturated, substituted or unsubstituted $C_6$ to $C_{22}$ hydrocarbon group, and n+m+w is from about 10 to 30.

9. The method of claim 8, wherein said blend is added to a weight concentration from 0.025% to 0.5%.

10. The method of claim 8 wherein the weight ratio of alkoxylated alcohol to ethoxylated sorbitan is from 1:99 to 99:1.

11. The method of claim 8 wherein the acid functional phenoxy herbicidal active is selected from the group consisting of phenoxy acetic acids, phenoxy propionic acids, phenoxy butyric acids and mixtures thereof.

12. The method of claim 8 wherein the weight ratio of alkoxylated alcohol to ethoxylated sorbitan is from 25:75 to 75:25.

13. The method of claim 8 wherein the weight ratio of alkoxylated alcohol to ethoxylated sorbitan is from 45:65 to 65:45.

* * * * *

UNITED STATES PATENT AND TRADEMARK OFFICE
CERTIFICATE OF CORRECTION

PATENT NO. : 8,673,819 B2
APPLICATION NO. : 13/002896
DATED : March 18, 2014
INVENTOR(S) : Jinxia Susan Sun It is certified that error appears in the above-identified patent and that said Letters Patent is hereby corrected as shown below:

In the Specification

Column 10, line 9, 10, "fluoroxypyr" -- should read -- fluroxypyr --.

Signed and Sealed this
Nineteenth Day of January, 2016

Michelle K. Lee
*Director of the United States Patent and Trademark Office*